(12) United States Patent
Ryan

(10) Patent No.: US 6,758,831 B2
(45) Date of Patent: Jul. 6, 2004

(54) DEVICE AND METHOD FOR ALIGNING WITH THE TUBAL OSTIUM

(75) Inventor: Thomas P. Ryan, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 166 days.

(21) Appl. No.: 09/961,917

(22) Filed: Sep. 24, 2001

(65) Prior Publication Data

US 2003/0060800 A1 Mar. 27, 2003

(51) Int. Cl.[7] .............................................. A61M 29/00
(52) U.S. Cl. ................................ 604/103.03; 606/193
(58) Field of Search ........................ 604/93.01, 96.01, 604/97.01, 97.02, 101.04, 102.02, 103.03, 104, 103.01; 606/192–194, 195, 197, 198; 128/831–836

(56) References Cited

U.S. PATENT DOCUMENTS

| | | | |
|---|---|---|---|
| 3,875,939 A | | 4/1975 | Bolduc et al. |
| 3,923,051 A | | 12/1975 | Soichet |
| 3,924,628 A | | 12/1975 | Droegemueller et al. |
| 4,016,867 A | | 4/1977 | King et al. |
| 4,121,572 A | | 10/1978 | Krzeminski |
| 4,182,328 A | | 1/1980 | Bolduc et al. |
| 4,204,548 A | | 5/1980 | Kurz |
| 4,642,101 A | * | 2/1987 | Krolikowski et al. .... 604/164.01 |
| 4,685,474 A | | 8/1987 | Kurz et al. |
| 4,764,845 A | | 8/1988 | Artus |
| 4,873,986 A | | 10/1989 | Wallace |
| 5,275,595 A | | 1/1994 | Dobak, III |
| 5,342,301 A | * | 8/1994 | Saab ...................... 604/103.13 |
| 5,449,380 A | | 9/1995 | Chin |
| 5,501,681 A | | 3/1996 | Neuwirth et al. |
| 5,520,682 A | | 5/1996 | Baust et al. |
| 5,647,868 A | | 7/1997 | Chinn |
| 5,868,735 A | | 2/1999 | Lafontaine |
| 5,891,457 A | | 4/1999 | Neuwirth |
| 5,902,251 A | | 5/1999 | vanHooydonk |
| 5,954,714 A | | 9/1999 | Saadat et al. |
| 5,964,755 A | | 10/1999 | Edwards |
| 6,026,331 A | | 2/2000 | Feldberg et al. |
| 6,066,132 A | | 5/2000 | Chen et al. |
| 6,080,129 A | * | 6/2000 | Blaisdell ...................... 604/515 |
| 6,216,704 B1 | | 4/2001 | Ingle et al. |

FOREIGN PATENT DOCUMENTS

WO    0054829    9/2000

OTHER PUBLICATIONS

Barbut, US Pub. No. 2002/0165573 A1.*
U.S. patent application Ser. No. 09/942,412, entitled, "Device and Method For Treating Intraluminal Tissue", filed Aug. 30, 2001, owned by Ethicon, Inc.
Internet publication entitled "Innovation—Thermachoice® Uterine Balloon Therapy System", by Johnson & Johnson, dated May 16, 2000.

* cited by examiner

Primary Examiner—Michael J. Hayes

(57) ABSTRACT

The present invention relates to an alignment device and method for facilitating alignment of a medical instrument with the tubal ostium of the Fallopian tubes. More particularly, the alignment device includes an expandable member, either in the form of a balloon member or sponge member, which is expandable from a contracted state to an expanded state by a fluid. In addition, the alignment device includes a catheter member attached to the expandable member and also includes, guiding means, in the form of passageways or the like, for guiding a medical instrument through the expandable member.

14 Claims, 7 Drawing Sheets

DEVICE AND METHOD FOR ALIGNING WITH THE TUBAL OSTIUM

FIELD OF THE INVENTION

The present invention relates to a device and method for facilitating alignment of a medical instrument within the tubal ostia of the Fallopian tubes. As used herein, the term "medical instrument" includes a medical or surgical instrument.

BACKGROUND OF THE INVENTION

There are various medical procedures that require doctors and surgeons to gain access to the Fallopian tubes by way of the transcervical, transvaginal access route into the uterus. Such medical procedures include patency testing of the Fallopian tubes, sterilization by tubal ligation or tubal occlusion, and fertilization procedures involving delivery of sperm into the Fallopian tubes. At the present time, several transcervical techniques are being developed to perform voluntary sterilization procedures by tubal occlusion using RF (radio frequency), microwave, implanted materials and chemical means. These transcervical sterilization techniques will replace surgical methods of sterilization, thereby allowing sterilizations to be performed more conveniently in doctors' offices or clinics, rather than in hospitals. These transcervical techniques, however, do not include a means by which their respective medical instruments can be aligned with the tubal ostium to facilitate a successful procedure.

To successfully perform the aforesaid medical procedures, doctors and surgeons must be able to guide the necessary instruments through the vagina and cervix, into the uterus and to the tubal ostium, i.e., the intrauterine opening of the Fallopian tubes. The diameter of each Fallopian tube at the tubal ostium is typically less than 1.0 millimeter. Thus, the most difficult part of the aforesaid medical procedures is often aligning an instrument with the tubal ostium such that the instrument will properly enter the Fallopian tube. Alternatively, proper alignment with the tubal ostium is important in certain procedures to ensure that dye, medicine or sperm will be properly delivered directly into the Fallopian tube, minimizing waste and maximizing the effectiveness of the procedure. Moreover, if such an insertion is attempted and fails, the Fallopian tube will often go into spasm and make subsequent attempts at entry much more difficult. It is, therefore, important that entry into the Fallopian tube during these medical procedures is successful on the first attempt, which, in turn, requires proper alignment with the tubal ostium.

Various methods exist to facilitate the alignment of medical instruments with the tubal ostium. For example, one method involves the transvaginal, transcervical insertion of a hysteroscope into the uterus to allow the doctor to visually align the medical instruments with the tubal ostium. This method, however, requires additional visualization equipment that is expensive and, in many Third World countries, prohibitively expensive. In addition, this method requires training and a skill level that many gynecologists may not possess.

Alignment devices, fluid dispensing instruments, uterine access catheter systems and the like are known for use within the female reproductive system. For example, U.S. Pat. No. 6,080,129 to Blaisdell discloses a catheter system for the uterus having a sleeve slidably disposed over an inner catheter. Initial access to the uterus is accomplished by positioning the inner catheter through the cervix with the sleeve remaining outside of the cervix. After inflating a balloon near the distal end of the inner catheter, contact media can be injected and hysterosalpinogography is performed.

U.S. Pat. No. 4,182,328 to Bolduc et al. discloses a fluid dispensing instrument for placing a drug material into the canals of the Fallopian tubes of a female. The instrument includes a housing carrying a piston and cylinder assembly which is operable to expand a balloon at its distal end, as well as to dispense drugs into the uterine cavity above the partly expanded balloon. The instrument is fully expanded to move the drugs from the uterine cavity into the canals of the Fallopian tubes.

In view of the foregoing, it is an object of the present invention to provide an alignment device for use by medical practitioners in blind medical procedures wherein the medical instrument is aligned with the tubal ostium of each Fallopian tube to facilitate a successful medical procedure within the Fallopian tubes without the use of an hysteroscopic instrument. Such an alignment device lends itself to use by medical personnel who need not have a high level of proficiency.

Another object of the present invention is to provide an alignment device that allows easy access of appropriate medical instruments to both right and left tubal ostium for the bilateral access, evaluation and/or treatment of each Fallopian tube.

Another object of the present invention is to provide an alignment device that eliminates the use of current visualization techniques using expensive hysteroscopic hardware and procedures by the gynecologists to evaluate a reproductive problem of a female patient.

Another object of the present invention is to provide an alignment device that will assist in transcervical sterilization (tubal ligation of the Fallopian tubes through the cervix and vagina) in order to assure accurate entry into the Fallopian tubes via the tubal ostia or tubal ostium.

Another object of the present invention is to provide an alignment device that will allow tubal patency testing to be done in a doctor's office without fluoroscopic procedures that irradiate the female patient and are normally performed in hospital settings.

Another object of the present invention is to provide an alignment device for use in Third World countries where fluoroscopic equipment and hysteroscopic visualization hardware may not be available.

Another object of the present invention is to provide an alignment device that will permit gynecologists, medical practitioners or trained clinic personnel to access the tubal ostia of the Fallopian tubes.

Another further object of the present invention is to provide an alignment device that is easy to use and is fully disposable after use.

A still further object of the present invention is to provide an alignment device that can be mass produced in an automated and economical manner and is readily affordable by the medical practitioner.

SUMMARY OF THE INVENTION

In accordance with the present invention, there is provided an alignment device adapted to deliver a medical instrument to an operating site within a body cavity. The alignment device includes a catheter member having an elongated body which is provided with a plurality of channels, at least one of the channels being sized and shaped so as to allow a medical instrument to pass through and at least another of the channels being sized and shaped so as to allow fluid to pass therethrough. The alignment device is also provided with an expandable member, which is expandable from a contracted state to an expanded state by fluid received from the catheter member. Guiding means, in the form of conduits, passageways, or the like, are located within the expandable member for guiding a medical instrument through the expandable member, when it is in its expanded state, to an operating site within a body cavity.

BRIEF DESCRIPTION OF THE DRAWINGS

Further objects, features and advantages of the present invention will become apparent upon the consideration of the following detailed description of the various exemplary embodiments considered in conjunction with the accompanying drawings, in which.

DETAILED DESCRIPTION OF A PREFERRED EMBODIMENT

Figures 1, 2, 3:
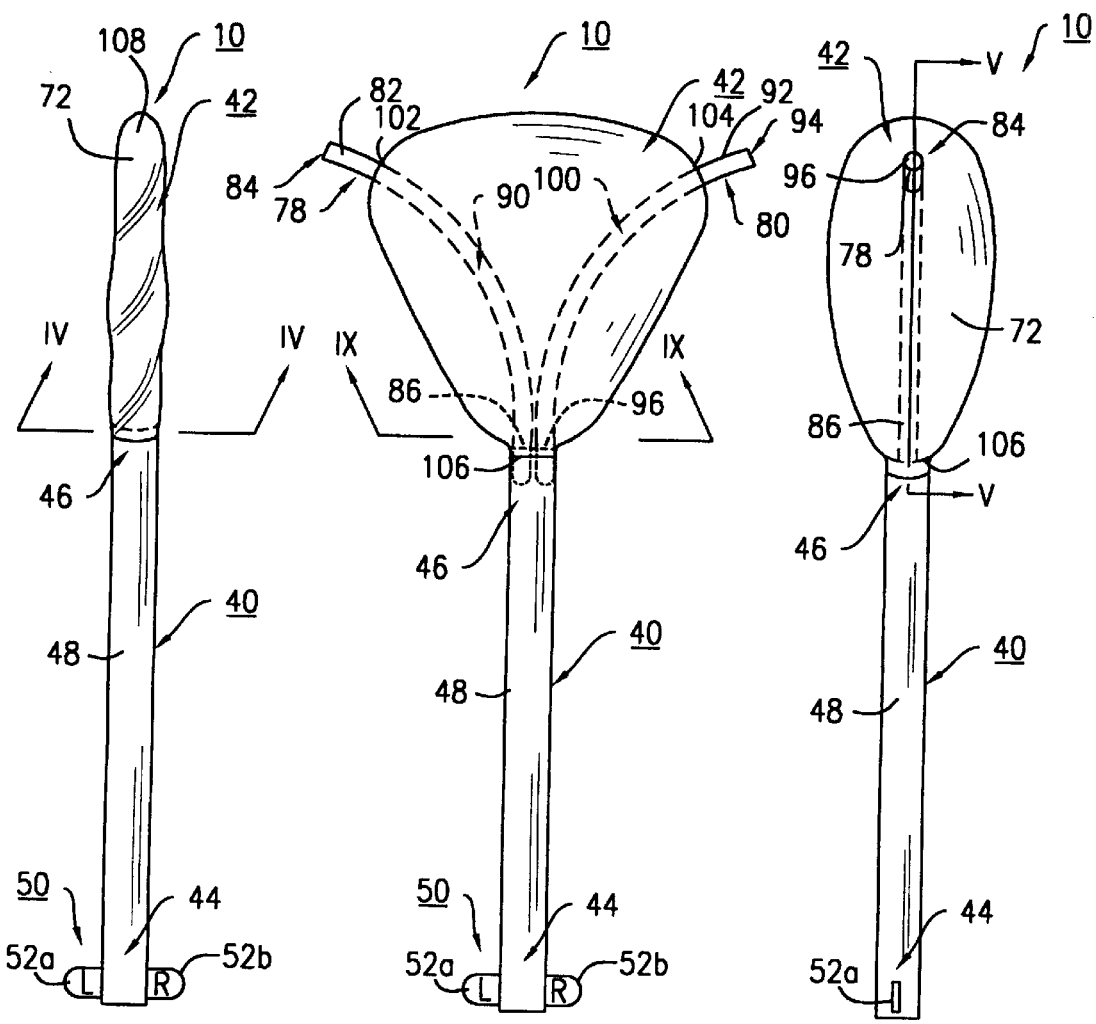
FIG. 1 is a front elevational view of an alignment device constructed in accordance with the present invention, which shows a balloon member in its deflated condition attached to a distal end of an associated catheter.
FIG. 2 is a view similar to the view of FIG. 1, except that the balloon member is shown in its inflated condition.
FIG. 3 is a side elevational view of the alignment device of FIGS. 1 and 2, which shows the balloon member in its inflated condition.
Figure 9:
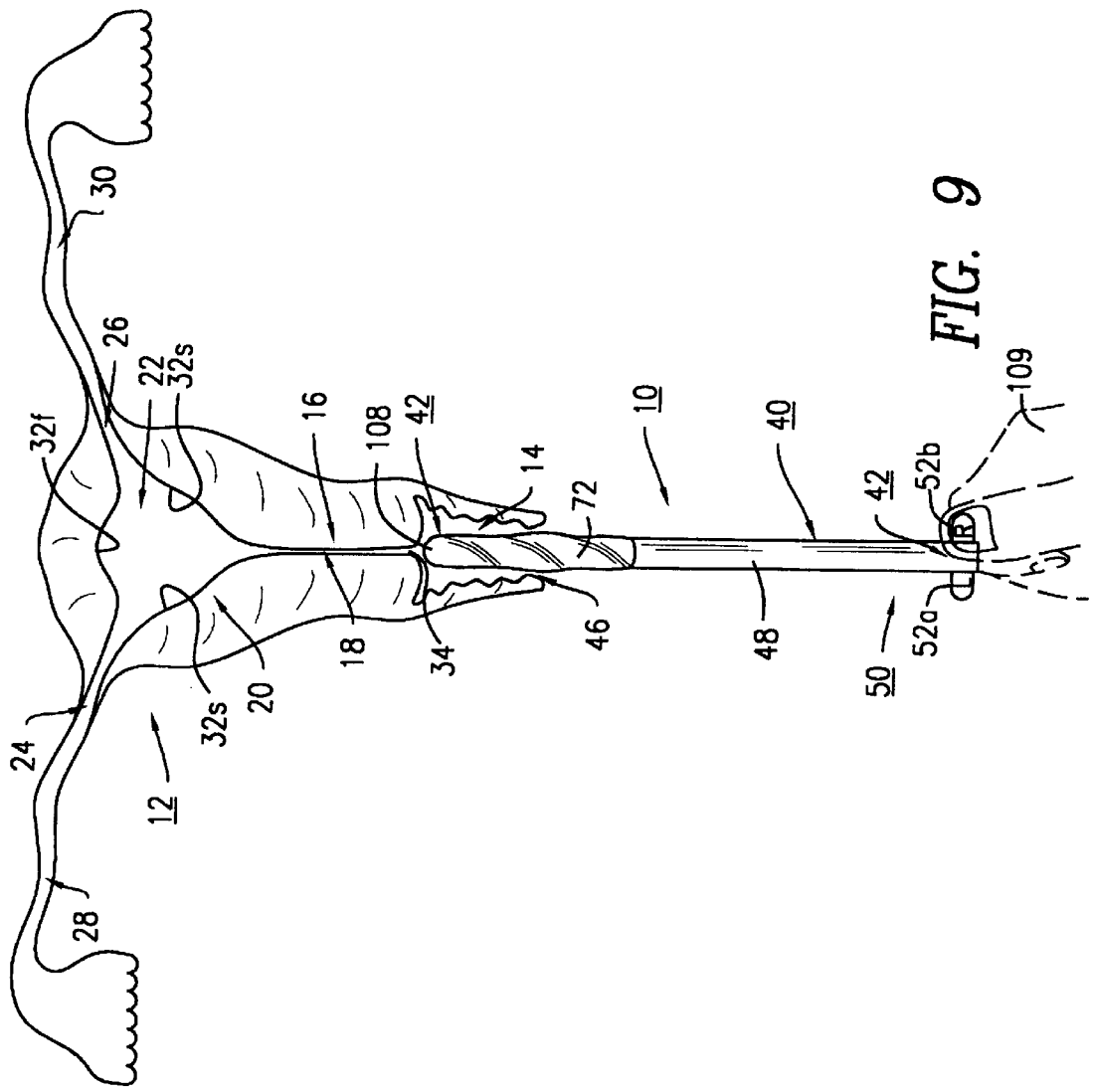
FIG. 9 is a schematic view of a female reproductive system and the alignment device of FIG. 5 which shows a tip portion of the alignment device inserted into a vaginal canal.

With reference to FIGS. 1 and 9, an alignment device 10 is shown which is adapted to be received within a human female reproductive system 12. In order to fully understand the advantages of the alignment device 10, a brief overview of the female reproductive system 12 is discussed below with reference to FIG. 9.

Figure 10:
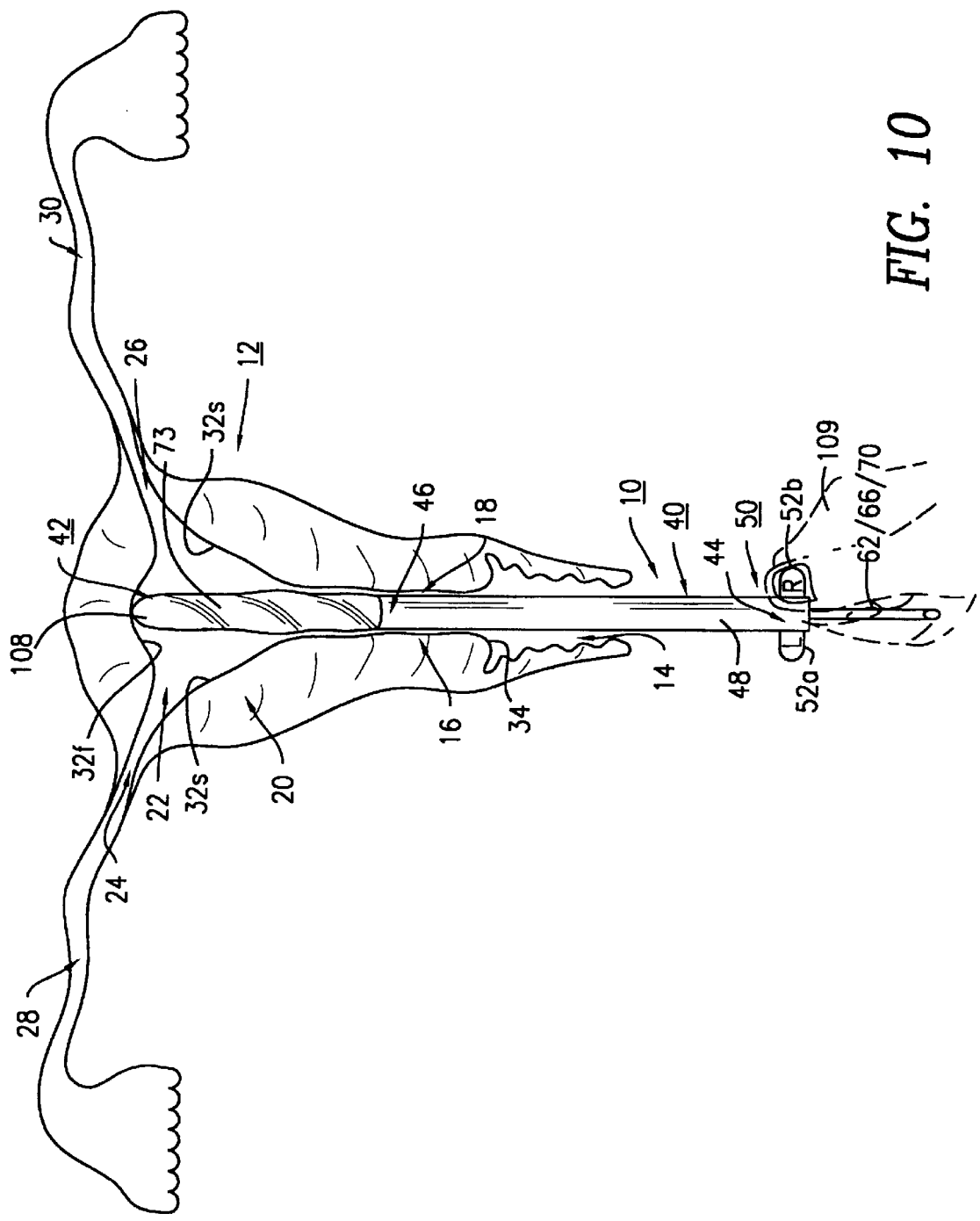
FIG. 10 is a view similar to the view of FIG. 9, except that the tip portion of the alignment device is shown in contact with an uterine cavity.

The female reproductive system 12 includes an elongated vaginal orifice 14, a cervix 16 having a cervical canal 18; an uterus 20 having an uterine cavity 22; tubal ostia 24, 26, and Fallopian tubes 28, 30. The Fallopian tubes 28, 30 are connected to the tubal ostia 24, 26, respectively, and include passageways which exit therefrom. The uterine cavity 22 is joined to the Fallopian tubes 28, 30 via their respective tubal ostia 24, 26, which can be enlarged and elongated as shown in FIG. 10. The cervical canal 18 is located between the lower part of the cervical cavity 18 and the upper end of the elongated vaginal orifice 14, and provides a passageway therebetween. As shown in FIG. 9, the cervical canal 18 has a normally closed entrance opening (external cervix os) 34.

The uterus 20 is a generally inverted pear-shaped, thick walled, hollow organ, which varies in size and shape, wall thickness, wall strength, and sensitivity to pain. The uterine cavity 22 is generally flat and triangularly-shaped, but other sizes and shapes can exist. Like the uterus 20, the size and shape of the uterine cavity 22 can also vary. The uterine cavity 22 includes a plurality of cavity walls in the form of a top wall (hereinafter referred to as a fundus 32f) and side walls 32s.

The cervix 16 includes muscles which vary in size and strength such that the insertion of the alignment device 10 through the cervical canal 18 may encounter some resistance. In such cases of cervical canal 18 resistance, a dilator (a surgical instrument or drug that produces dilation of the cervical canal 18) is typically used to open the cervical canal 18 to an opening size of approximately 6 mm in diameter prior to the insertion of the alignment device 10 therein.

With reference to FIG. 1, the alignment device 10 includes a sheath or tube component in the form of a catheter 40 and a balloon member 42 attached thereto. The balloon member 42 is adapted to inflate into a fully expanded configuration as shown in FIG. 2 and to deflate into a fully collapsed configuration as shown in FIG. 1.

The catheter 40 is made from a material, such as stainless steel, teflon or silicone, having a range of stiffness from rigid to flexible, and has a length in a range of from about 120 mm to about 140 mm and a diameter in a range of from about 4 mm to about 8 mm. As shown in FIG. 1, the catheter 40 includes a proximal end 44, a distal end 46 attached to the balloon member 42, and an exterior wall surface 48. The proximal end 44 of the catheter 40 includes a positioning assembly 50 which has opposing left and right positioning tabs 52a, 52b attached to the exterior wall surface 48, and which orient and position the balloon member 42 as will be described more fully hereinafter.

Figure 4:
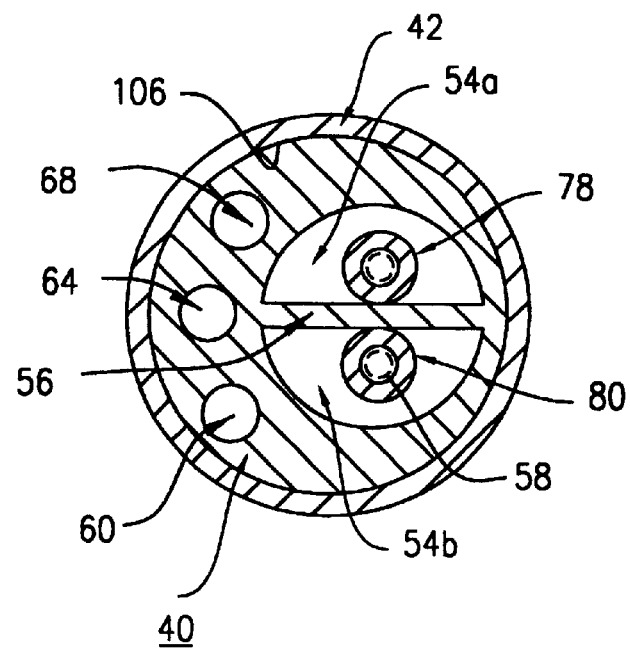
FIG. 4 is an enlarged cross-sectional view, taken along section lines IV—IV and looking in the direction of the arrows, of the alignment device of FIG. 1.

With reference to FIG. 4, the catheter 40 includes a pair of interior passageways 54a, 54b divided by a wall 56. Each of the passageways 54a, 54b is sized and shaped to allow a medical instrument 58 (shown schematically and in phantom in both of the passageways) to pass therethrough. A passageway 60 is provided for receiving air, via an air line 62 (see FIG. 10), while a passageway 64 is provided for receiving liquid (e.g., water or a saline solution), via a fluid line 66 (see FIG. 10). Either the air supplied via the passageway 60 or the liquid supplied via the passageway 64 can be used to inflate the balloon member 42 (see FIG. 1) to its fully inflated configuration as shown in FIG. 2. Further, a passageway 68 is provided for receiving a vacuum, via a vacuum line 70 (FIG. 10), to evacuate the air or liquid from the balloon member 42 (FIG. 1), thereby causing it to deflate and assume its fully collapsed configuration as shown in FIG. 1, whereby the alignment device 10 can be removed from the uterine cavity 22 (see FIG. 9). Any one of the passageways 60, 64, 68 can have a pressure gauge (not shown) attached thereto for gauging the internal inflation pressure of the balloon member 42. Alternatively, the catheter 40 may have a single passageway (not shown) that can receive air, fluid, and vacuum, rather than having the three separate passageways 60, 64, 68.

Figure 5:
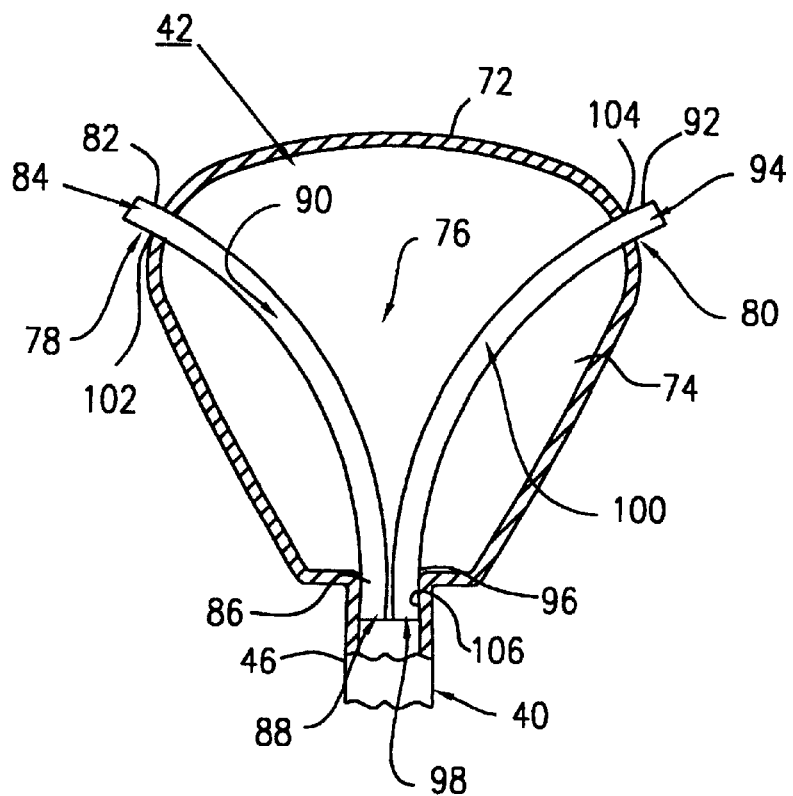
FIG. 5 is a cross-sectional view, taken along section lines V—V and looking in the direction of the arrows, of the alignment device of FIG. 3.

When inflated as shown in FIG. 5, the balloon member 42 has a substantially triangularly-shaped or pear-shaped configuration which complements the shape of the uterine cavity 22 (see FIG. 11), and includes an exterior wall surface 72, an interior wall surface 74, and an interior chamber 76 filled with air, water or saline solution. The balloon member 42 further includes a first tube member 78 and a second tube member 80, both of which are positioned within the interior chamber 76. When the balloon member 42 is in its fully collapsed configuration, the tube members 78, 80 are sized and shaped to allow them to be twisted around the balloon member 42 and therefore substantially concealed from view. The first tube member 78 includes a distal end 82, relative to the catheter 40, which has an opening 84. In addition, the first tube member 78 includes a proximal end 86, relative to the catheter 40 (see FIG. 1), which has an opening 88. A passageway 90 extends through the first tube member 78 from the distal end 82 to the proximal end 86. The passageway 90 is sized and shaped to allow a medical instrument to pass therethrough.

The second tube member 80, like the first tube member 78, includes a distal end 92, relative to the catheter 40, which has an opening 94. In addition, the second tube member 80 includes a proximal end 96, relative to the catheter 40, which has an opening 98. A passageway 100 extends through the second tube member 80 from the distal end 92 to the proximal end 96. The passageway 100 is sized and shaped to allow a medical instrument to pass therethrough.

The balloon member 42 has an opening 102 sized and shaped to allow the distal end 82 of the first tube member 78 to extend therethrough, an opening 104 sized and shaped to allow the distal end 92 of the second tube member 80 to extend therethrough, and an opening 106 sized and shaped to allow the distal end 46 of the catheter 40 to be received therein. As shown in FIG. 5, the distal ends 82, 92 of the first and second tube members 78, 80, respectively, extend slightly from their respective tube openings 102, 104 of the balloon member 42 so as to allow the distal ends 82, 92 to cooperate and align with the tubal ostia 24, 26, respectively (see FIG. 11). Alternatively, the distal ends 82, 92 of the tube members 78, 80 do not have to extend beyond their respective tube openings 102, 104 of the balloon member 42. In other words, the distal ends 82, 92 can lie in the same plane as, and can be adjacent to, their respective tube openings 102, 104.

Figure 11:
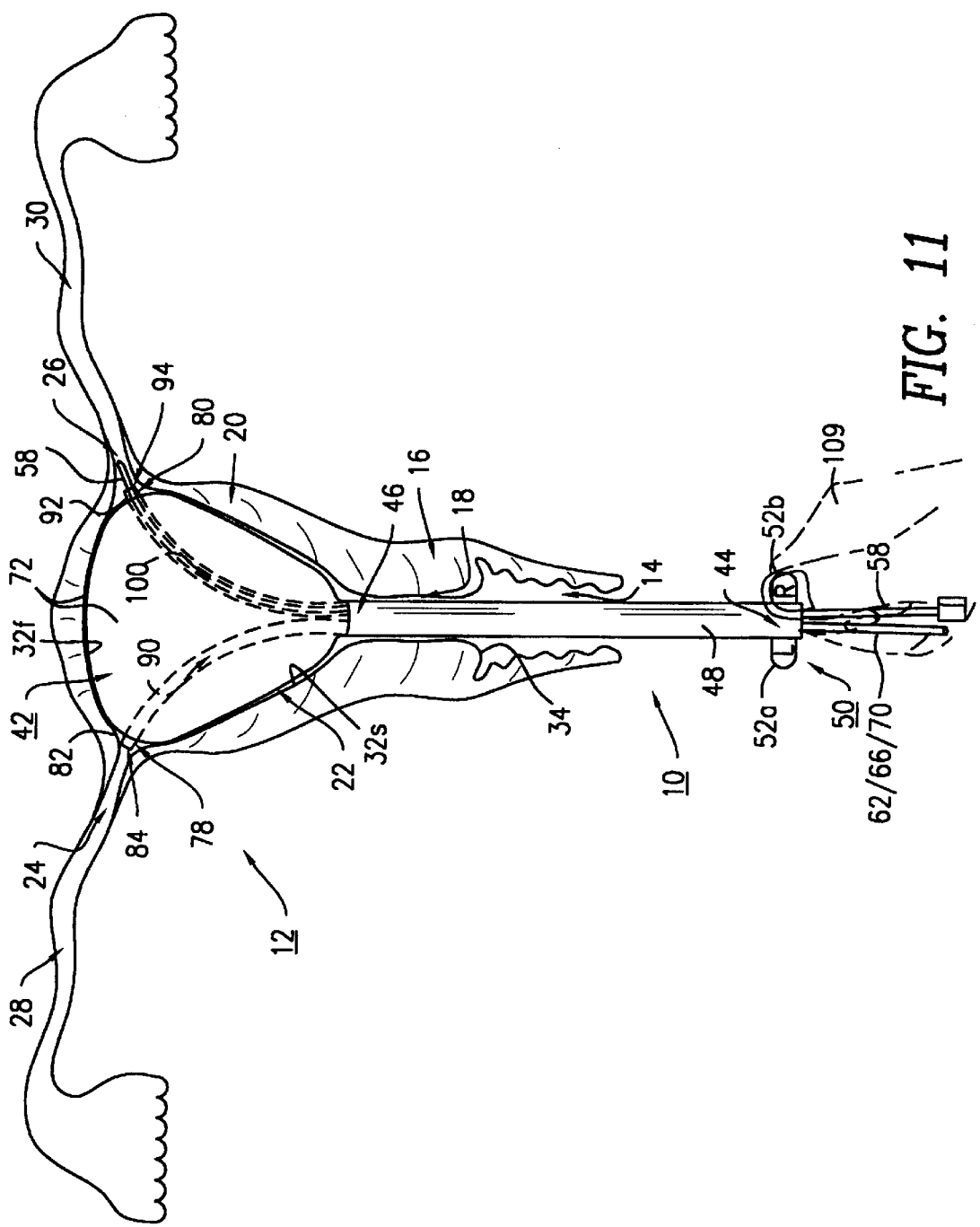
FIG. 11 is a view similar to the view of FIG. 10, except that the balloon member of the alignment device is shown in its inflated condition.

The left and right positioning tabs 52a, 52b (see FIG. 1) orient and position the balloon member 42 prior to inflation, such that the tube openings 84, 94 of the tube members 78, 80 align with and are adjacent to the tubal ostia 24, 26, respectively, when the balloon member 42 is fully inflated as depicted in FIG. 11. The distal ends 82, 92 of the first and second tube members 78, 80 are attached to their respective first and second tube openings 102, 104 via attachment means, such as conventional adhesives and glues, laser bonding, ultrasonic welding and epoxies, etc.

As shown in FIG. 5, the proximal ends 86, 96 of the tube members 78, 80, respectively, extend slightly from the opening 106 of the balloon member 42. Alternatively, the proximal ends 86, 96 of the tube members 78, 80 can be sized and shaped so as to not extend beyond the opening 106 of the balloon member 42. In other words, the proximal ends 86, 96 lie in the same plane as, and are adjacent to, the opening 106.

The proximal ends 86, 96 of the tube members 78, 80 are received and cooperate with the passageways 54a, 54b (FIG. 4), respectively, in the catheter 40 (FIG. 1). Further, the proximal ends 86, 96 of the tube members 78, 80 are adjacent and connected to each other.

The opening 106 of the balloon member 42 is attached and connected to the distal end 46 of the catheter 40, as shown in FIG. 5. Also, the tube members 78, 80 are aligned in a planar relationship with each other and their respective distal ends 82, 92 being arranged approximately 180 degrees apart.

When inflated, the balloon member 42 is sized and shaped such that the tube openings 84, 94 align with, and are adjacent to, the tubal ostia 24, 26 (see FIG. 11), respectively. The balloon member 42 can be made from a material which is selected from a group including silicone, latex, urethane, and other flexible polymers. When fully inflated with air, the balloon member 42 has a width in a range of from about 30 mm to about 40 mm, a height in a range of from about 50 mm to about 70 mm, a depth in a range of from about 10 mm to about 15 mm, and a pressure in a range of from about 150 mm Hg to about 250 mm Hg, as determined by the air line 62 (FIG. 11) which is connected to a syringe 107 (see FIG. 8).

Each tube member 78, 80 (see FIG. 5) can be made from a material which is selected from a group including nylon, polyethylene, teflon, silicone, tygon, and other flexible polymers. In addition, each opening 84, 88, 94, 98 (FIG. 5) has a diameter in a range of from about 1 mm to about 3 mm.

Operation of the Present Invention

With reference to FIG. 9, after dilating the cervical canal 18, the alignment device 10 is initially inserted into the vaginal canal 14 until a tip portion 108 of the balloon member 42 enters the external cervical os 34 area. Note that in the foregoing step, the balloon member 42 is not inflated.

As shown in FIG. 10, the alignment device 10 is then guided through the vaginal canal 14, the cervical canal 18, and into the uterine cavity 22 such that the tip portion 108 of the balloon member 42 is in contact with the top wall (fundus) 32f of the uterine cavity 22. Next, the catheter 40 is oriented and positioned within the cervical canal 18 via the positioning tabs 52a, 52b to properly align the balloon member 42 within the uterine cavity 22.

The balloon member 42 is then fully inflated with air, via the air line 62 (see FIG. 11) and the passageway 60 (see FIG. 4) of the catheter 40, such that the openings 84, 94 of the tube members 78, 80 align and cooperate with the tubal ostia 24, 26 of their respective Fallopian tubes 28, 30 as shown in FIG. 11. When inflated, the exterior wall surface 72 of the balloon member 42 is in full contact with the top wall 32f and the side walls 32s of the uterine cavity 22. In this position, the distal tube openings 84, 94 are properly oriented with the tubal ostia 24, 26, respectively.

With the alignment device 10 in place, a medical practitioner 109 (a hand thereof being shown in FIGS. 9–11) can proceed to perform a surgical or medical procedure within at least one of the Fallopian tubes 28, 30. The medical instrument 58 is inserted into and guided through a corresponding one of the passageways 54a, 54b (see FIG. 4) of the catheter 40. Next, the medical instrument 58 is maneuvered and guided through a corresponding one of the tube passageways 90, 100 (see FIG. 11), and finally exits through a corresponding one of the distal openings 84, 94.

Thereafter, the medical instrument 58 enters a corresponding one of the tubal ostia 24, 26 to complete the treatment. After the treatment is completed, the medical instrument 58 is removed from the catheter 40 in the opposite order as previously described. Then, the balloon member 42 of the alignment device 10 is removed from the reproductive system 12 by initially collapsing it via vacuum, via the vacuum line 70, through the passageway 68 (see FIG. 4). Lastly, the alignment device 10 is removed from the uterine cavity 22, the cervical canal 18, and the vaginal orifice 14 and can be medically disposed with in accordance to standard medical protocols.

Description of the Alternate Embodiments

Figure 6:
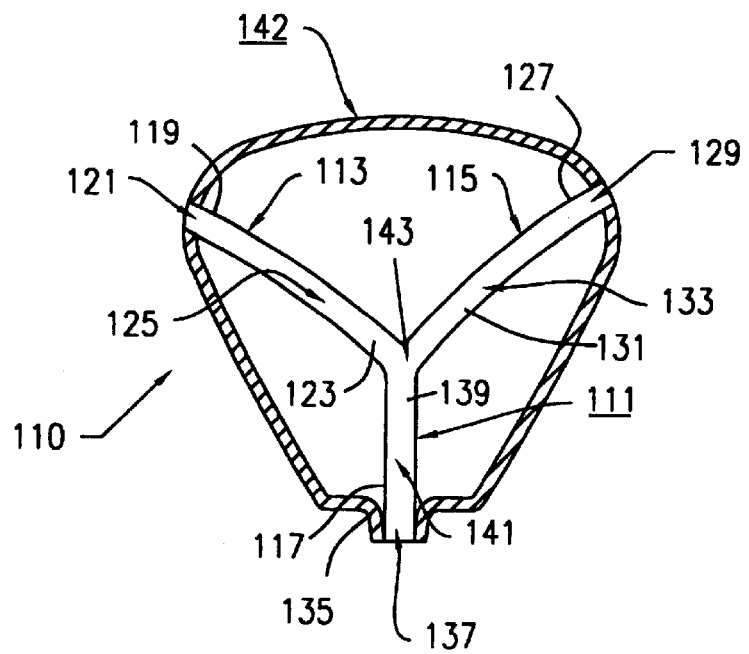
FIG. 6 is a cross-sectional view, similar to that of FIG. 5, of an alignment device in accordance with a second exemplary embodiment of the present invention.

A second exemplary embodiment of the present invention is illustrated in FIG. 6. Elements illustrated in FIG. 6 which correspond to the elements described above with reference to FIG. 5 have been designated by corresponding reference numerals increased by one hundred. In addition, elements illustrated in FIG. 6 which do not correspond to the elements described above with reference to FIG. 5 have been designated by odd numbered reference numerals starting with reference number 111. The embodiment of FIG. 6 operates in the same manner as the embodiment of FIG. 5, unless it is otherwise stated.

FIG. 6 shows an alignment device 110 having a balloon member 142, which includes a single Y-shaped tubing member 111, replacing the first and second tube members 78, 80 (see FIG. 5) of the balloon member 42. The Y-shaped tubing member 111 includes a first tube arm 113, a second tube arm 115, and a third tube arm 117. The first tube arm 113 includes a distal end 119 with an opening 121 and an inner end 123, which is opposite the distal end 119. A passageway 125 is included between the distal end 119 and the inner end 123. Likewise, the second tube arm 115 includes a distal end 127 with an opening 129 and an inner end 131, which is opposite the distal end 127. A passageway 133 is included between the distal end 127 and the inner end 131. The third tube arm 117 includes a proximal end 135 with an opening 137 and an inner end 139, which is opposite the proximal end 135. A passageway 141 is included between the proximal end 135 and the inner end 139. The inner ends 123, 131, and 139 of the tube arms 113, 115, and 117, respectively, are joined together at a connecting junction 143 so as to form the Y-shaped configuration of the tubing member 111.

Figure 7:
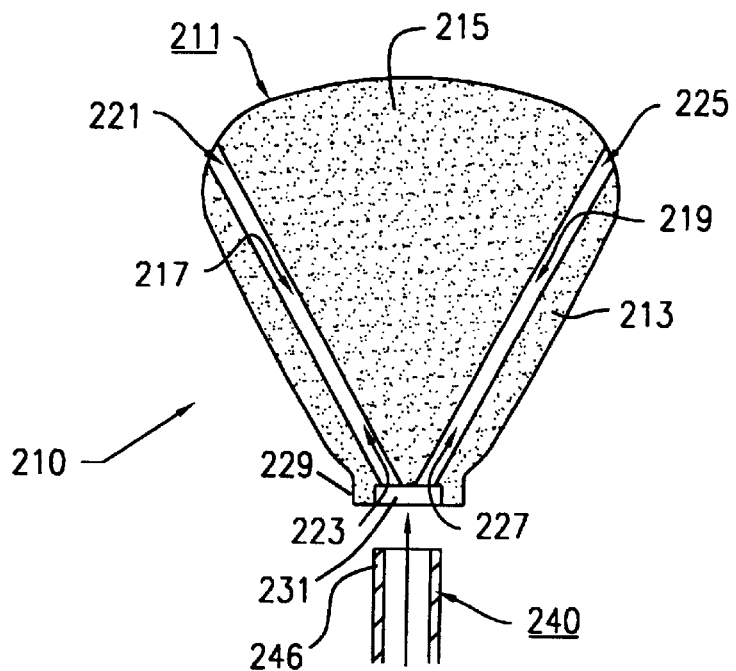
FIG. 7 is an exploded, cross-sectional view, similar to that of FIG. 5, of an alignment device in accordance with a third exemplary embodiment of the present invention.

A third exemplary embodiment of the present invention is illustrated in FIG. 7. Elements illustrated in FIG. 7 which correspond to the elements described above with reference to FIG. 5 have been designated by corresponding reference numerals increased by two hundred. In addition, elements illustrated in FIG. 7 which do not correspond to the elements described above with reference to FIG. 5 have been designated by odd numbered reference numerals starting with reference number 211. The embodiment of FIG. 7 operates in the same manner as the embodiment of FIG. 5, unless it is otherwise stated.

FIG. 7 shows an alignment device 210 having a sponge member 211, replacing the balloon member 42 used by the alignment device 10. The sponge member 211 is adapted to contract between a collapsed configuration by standard vacuum processes and an expanded configuration by a fluid as shown in FIG. 7. Also, the sponge member 211 includes an exterior wall surface 213 and a sponge body 215 which has a first passageway 217 and a second passageway 219 extending therethrough. The passageways 217, 219 are pre-drilled or die cut in a linear or curvilinear fashion through the sponge body 215 prior to the attachment to a catheter 240. The first passageway 217 includes a distal opening 221 and a proximal opening 223 relative to the catheter 240, while the second passageway 219 includes a distal opening 225 and a proximal opening 227 relative to the catheter 240. A proximal end 229 of the sponge body 215 includes a catheter receiving cavity 231 sized and shaped to allow a distal end 246 of the catheter 240 to be received therein.

The operation of the alignment device 210 is similar and operates in the same manner as the alignment device 10. However, the alignment device 210 is expanded in a different manner than the alignment device 10. That is, the sponge member 211 expands in response to the absorption of liquid by the sponge body 215.

Figure 8:
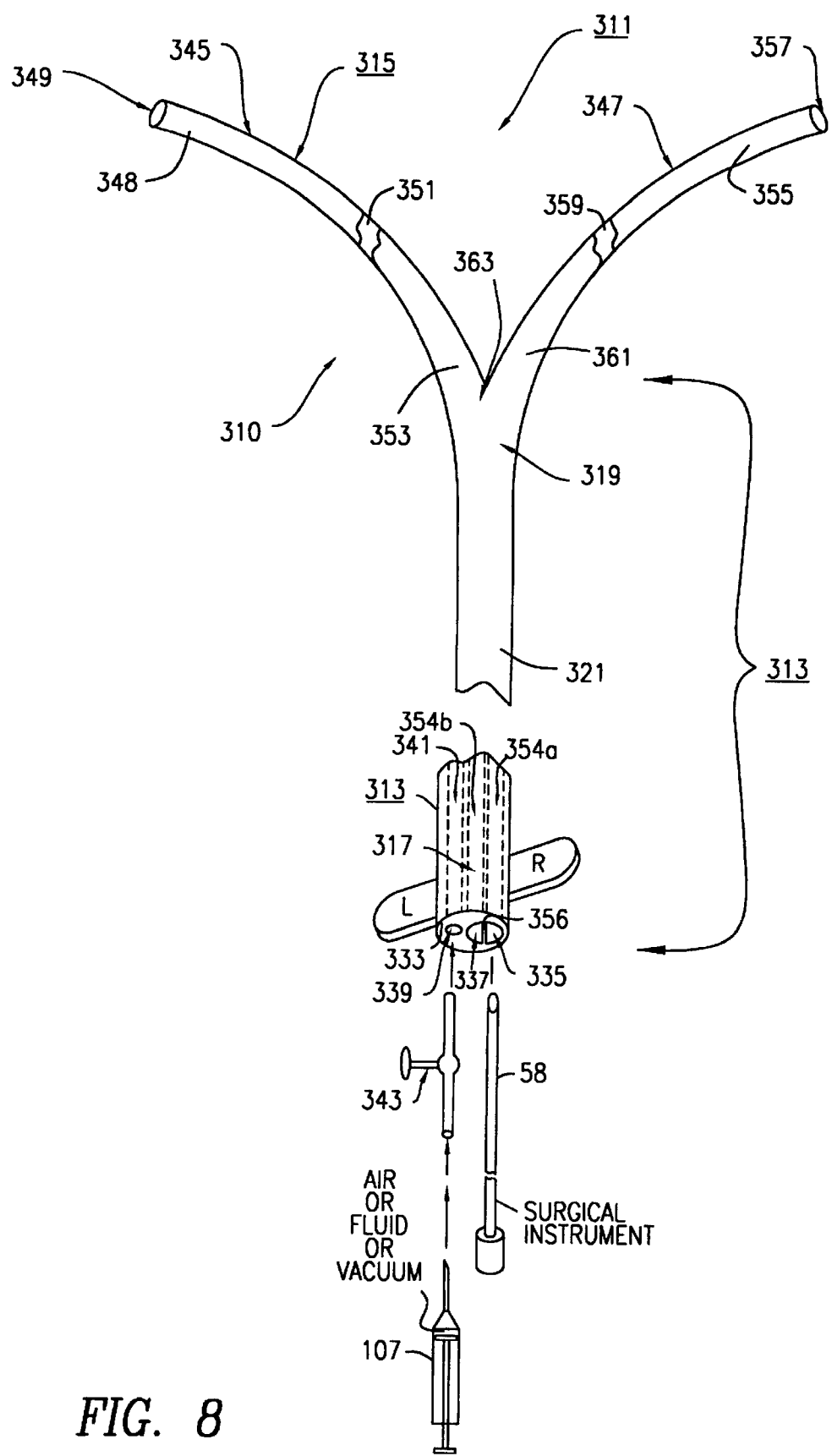
FIG. 8 is an exploded perspective view of an alignment device constructed in accordance with a fourth exemplary embodiment of the present invention.

A fourth exemplary embodiment of the present invention is illustrated in FIG. 8. Elements illustrated in FIG. 8 which correspond to the elements described above with reference to FIG. 5 have been designated by corresponding reference numerals increased by three hundred. In addition, elements illustrated in FIG. 8 which do not correspond to the elements described above with reference to FIG. 5 have been designated by odd numbered reference numerals starting with reference number 311. The embodiment of FIG. 8 operates in the same manner as the embodiment of FIG. 5, unless it is otherwise stated.

FIG. 8 shows an alignment device 310 having an integrated, unitary tube-catheter member 311, which replaces the tube members 78, 80 (FIG. 5) and the catheter 40 (FIG. 1) of the alignment device 10. The tube-catheter member 311 includes a catheter section 313 and an integrally connected V-shaped tube section 315. The catheter section 313 includes a proximal end 317, a distal end 319, and an exterior wall surface 321. As shown in FIG. 8, the proximal end 317 includes a rear end wall 333 with two D-shaped lumen openings 335, 337 which lead to a pair of interior passageways 354a, 354b divided by a wall 356 therebetween. The passageways 354a, 354b are sized and shaped to allow the medical instrument 58 to pass therethrough. A channel opening 339 (e.g., a receiving port) is provided for discharging the incoming inflating air into a balloon member (not shown) and leads to a passageway 341. The channel opening 339 is connected to a stopcock 343 adapted to receive fluid (air, water or saline solution) from the syringe 107 for inflating the balloon member (not shown) to a fully inflated state and further adapted to receive vacuum from the syringe 107 for deflating the balloon member to a collapsed state.

As illustrated in FIG. 8, the V-shaped tube section 315 includes a first tube arm 345 and a second tube arm 347. The first tube arm 345 includes a distal end 348, which has an opening 349. A passageway 351 is included in the first tube arm 345 and has an inner end 353. Like the first tube arm 345, the second tube arm 347 includes a distal end 355, which has an opening 357. A passageway 359 is included in the second tube arm 347 and has an inner end 361. The inner ends 353, 361 of the tube arms 345, 347 and the distal end 319 of the catheter section 313 are integrally joined together at a junction 363.

The tube-catheter member 311 can be made from a polymer material which is selected from a group including nylon, teflon, polyethylene, silicone, tygon, and other flexible polymers. The catheter section 313 has a diameter in a range of from about 4 mm to about 8 mm and a length in a range of from about 150 mm to about 250 mm. When collapsed, the balloon member (not shown) has a length in a range of from about 50 mm to about 60 mm.

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

What is claimed is:

1. An alignment device adapted to deliver a medical instrument to an operating site within a body cavity, comprising a catheter member having a proximal end and a distal end, said catheter member including an elongated body having a plurality of channels extending from said proximal end to said distal end, at least one of said channels being sized and shaped so as to allow a medical instrument to pass therethrough and at least another of said channels being sized and shaped so as to allow a fluid to pass therethrough; an expandable member having at least one entrance portal attached to said distal end of said catheter, said expandable member also having a plurality of openings remote from said entrance portal and including a first opening and a second opening, said expandable member being expandable from a contracted state to an expanded state when a fluid is supplied thereto; and guiding means entering said expandable member through said at least one entrance portal for guiding a medical instrument through said expandable member when said expandable member is in its said expanded state, said guiding means including a plurality of tube members extending through said expandable member, said plurality of tube members including a first tube member communicating with the environment external to the alignment device through said first opening and a second tube member communicating with the environment external to the alignment device through said second opening.

2. An alignment device in accordance with claim 1, wherein said expandable member is expandable to its said expanded state when a fluid is passed through said at least another of said channels.

3. An alignment device in accordance with claim 1, wherein said expandable member is collapsible to its said contracted state when a vacuum is supplied to said expandable member through said at least another of said channels.

4. An alignment device in accordance with claim 1, wherein said expandable member is a balloon member.

5. An alignment device in accordance with claim 4, wherein each of said first and second tube members includes a passageway which is sized and shaped so as to allow a medical instrument to pass therethrough.

6. An alignment device in accordance with claim 4, wherein said guiding means includes a substantially Y-shaped tube member within said balloon member, said tube member including a first tube arm, a second tube arm, and a third tube arm connected to said first tube arm and to said second tube arm.

7. An alignment device in accordance with claim 4, wherein guiding means includes a plurality of tube arms integrally connected to said distal end of said catheter member.

8. An alignment device in accordance with claim 4, wherein said distal end of said catheter member is attached to said expandable member by attachment means.

9. An alignment device in accordance with claim 8, wherein said attachment means includes ultrasonic welding.

10. An alignment device in accordance with claim 1, wherein said expandable member is a sponge member.

11. An alignment device in accordance with claim 10, wherein said guiding means includes a plurality of passageways within said sponge member.

12. An alignment device in accordance with claim 11, wherein said sponge member includes a cavity which is sized and shaped so as to allow said distal end of said catheter member to be received therein.

13. An alignment device in accordance with claim 1, further comprising positioning means attached to said proximal end of said catheter member for positioning said expandable member when said expandable member is in its said contracted state.

14. An alignment device in accordance with claim 13, wherein said positioning means includes a pair of positioning tabs.

* * * * *